United States Patent [19]  [11] 4,097,595
Heymés  [45] Jun. 27, 1978

[54] 7-AMINO-THIAZOLYL ACETAMIDO CEPHALOSPORANIC ACIDS
[75] Inventor: René Heymés, Romainville, France
[73] Assignee: Roussel Uclaf, Paris, France
[21] Appl. No.: 758,634
[22] Filed: Jan. 12, 1977
[30] Foreign Application Priority Data
Jan. 14, 1976  France ............................... 76 00843
[51] Int. Cl.² ................ C07D 501/36; A61K 31/545
[52] U.S. Cl. ..................................... 424/246; 544/26; 544/27
[58] Field of Search ................... 260/243 C; 424/246; 544/26, 27
[56] References Cited
U.S. PATENT DOCUMENTS
3,886,150  5/1975  Sellstedt et al. ................ 260/243 C
3,926,984  12/1975  Teller et al. .................... 260/243 C
FOREIGN PATENT DOCUMENTS
2,255,077  7/1975  France ................................. 424/246

Primary Examiner—Nicholas S. Rizzo
Attorney, Agent, or Firm—Hammond & Littell

[57] ABSTRACT
Novel 7-amino-thiazolyl-acetamido-cephalosporanic acid compounds of the formula

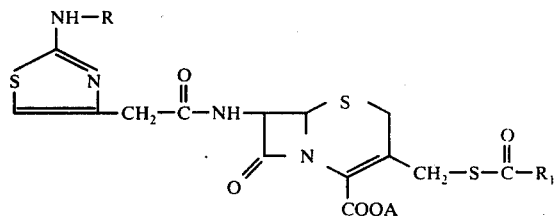

wherein R is selected from the group consisting of hydrogen and a group easily removable by acid hydrolysis or hydrogenolysis, $R_1$ is selected from the group consisting of alkyl of 1 to 4 carbon atoms, a 5 member heterocyclic ring and a 5 member heterocyclic ring containing a ketone group and A is selected from the group consisting of hydrogen, alkali metal and equivalents of alkaline earth metals, magnesium and organic amine having antibiotic activity against gram negative and gram positive bacteria and their preparation and novel intermediates therefore.

15 Claims, No Drawings

7-AMINO-THIAZOLYL ACETAMIDO CEPHALOSPORANIC ACIDS

STATE OF THE ART

French Pat. No. 2,255,077 of Takeda describes antibacterial cephalosporins having a different substitutent in the 3-position.

OBJECTS OF THE INVENTION

It is an object of the invention to provide the novel cephalosporanic acid compounds of formula I.

It is another object of the invention to provide a novel process for the preparation of the compounds of formula I and novel intermediates therefore.

It is a further object of the invention to provide novel antibiotic compositions and a novel method of combatting bacterial infections in warm-blooded animals, including humans.

These and other objects and advantages of the invention will become obvious from the following detailed description.

THE INVENTION

The novel final products of the invention are 7-amino-thiazolyl-acetamido-cephalosporanic acid compounds of the formula

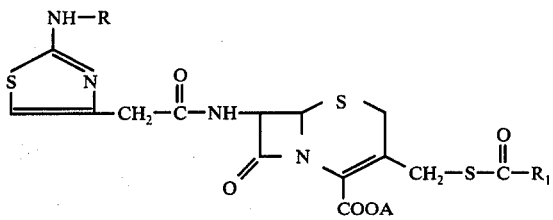

wherein R is selected from the group consisting of hydrogen and a group easily removable by acid hydrolysis or hydrogenolysis, $R_1$ is selected from the group consisting of alkyl of 1 to 4 carbon atoms, a 5 member heterocyclic ring and a 5 member heterocyclic ring containing a ketone group and A is selected from the group consisting of hydrogen, alkali metal and equivalents of alkaline earth metals, magnesium and an organic amine.

Groups that are easily removable by acid hydrolysis or hydrogenolysis are well known in cephalosporin chemistry and include tert.-butoxy carbonyl, trityl, benzyl, dibenzyl, trichloroethyl, carbobenzyloxy, formyl and phthaloyl.

Examples of $R_1$ are methyl, ethyl, propyl, isopropyl, butyl, sec-butyl, tert.-butyl, furyl, thiazolyl, oxothiazolinyl, isothiazolyl, oxazolyl, imidazolyl, diazolyl, thiadiazolyl and tetrazolyl. Examples of A are hydrogen, sodium, potassium, lithium, calcium and magnesium and organic amines such as triethylamine, trimethylamine, methylamine, propylamine, N,N-dimethyl ethanolamine or tris(hydroxymethyl)methylamine.

Among the preferred compounds of formula I, R is tert.-butoxycarbonyl, trityl, dibenzyl, trichloroethyl and carbobenzyloxy. Preferably R is hydrogen or trityl and $R_1$ is methyl, ethyl, furyl or 2-oxo (3H) thiazolin-4-yl and A is hydrogen. The most preferred compound is 7-[2-(2-amino-4-thiazolyl)-acetamido]-3-acetylthiomethyl-ceph-3-eme-4-carboxylic acid.

The novel products can exist in the form of formula I or in the following formula

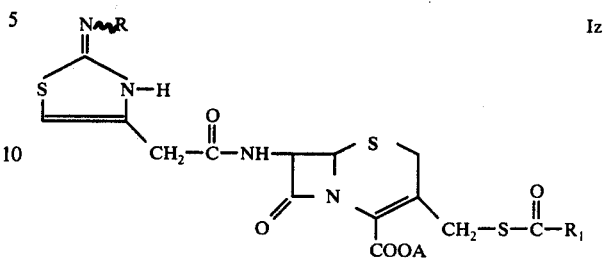

wherein R, $R_1$ and A have the above definitions.

The process of the invention for the production of compounds of formula I comprises reacting a compound of the formula

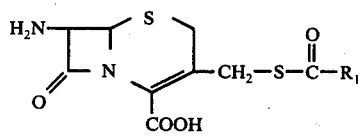

wherein $R_1$ has the above definition with an acid of the formula

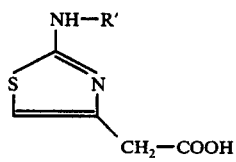

or a functional derivative thereof wherein R' is a group easily removable by acid hydrolysis or hydrogenolysis to obtain a compound of the formula

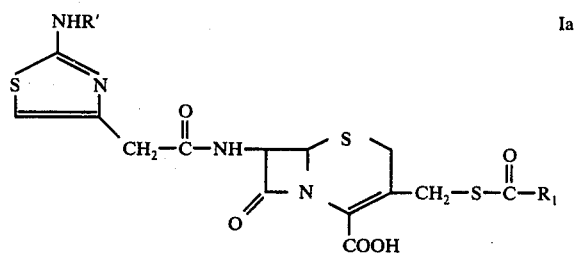

which is a compound of formula I wherein R is other than hydrogen and A is hydrogen and the said product may be treated with an acid media or subjected to hydrogenolysis to obtain the corresponding compound of formula $I_b$ which is a compound of formula I, wherein R is hydrogen and if desired the product Ia or Ib may be salified with a mineral or organic base or amine to obtain the compounds of formula I where A is other than hydrogen.

In a modification of the process of the invention, a compound of the formula

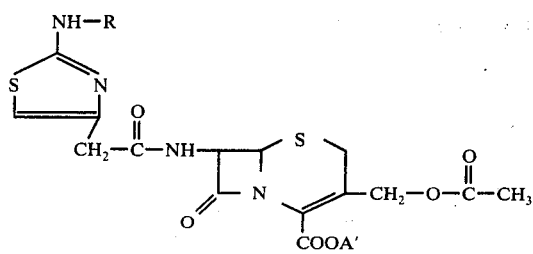

wherein R has the above definition and A' is hydrogen or an alkali metal is reacted with a compound of the formula

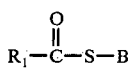

wherein $R_1$ has the above definition and B is hydrogen or an alkali metal to obtain the corresponding compound of formula I wherein A is hydrogen or an alkali metal which if salified may be treated with an acid to obtain the free acid.

In a preferred mode of the first process described above, the compound of formula II is reacted with a functional derivative of the acid of formula III such as the acid chloride or acid anhydride. The acid anhydride may be formed in situ by action of isobutyl chloroformate on the free acid. Other acid halides or other acid anhydrides formed in situ by reaction with other alkyl chloroformates, a dialkylcarbodiimide or a dicycloalkylcarbodiimide such as dicyclohexylcarbodiimide can be used. Equally useful are other acid derivatives such as the azide, amide or ester of the acid formed such as with hydroxy succinimide, p-nitrophenol or 2,4-dinitrophenol.

If the compound of formula II is reacted with the acid halide of the acid of formula III or an anhydride formed with isobutyl chloroformate, the reaction is preferably effected in the presence of a basic agent such as an alkali metal carbonate or a tertiary organic base such as N-methylmorpholine, pyridine or a trialkylamine such as triethylamine.

The acid hydrolysis agent to form the compounds of formula Ib may be an acid such as trifluoroacetic acid, formic acid or acetic acid. These acids can be used in an anhydrous or aqueous medium. A preferred agent for hydrogenolysis is zinc-acetic acid system. The preferred hydrolysis agent to remove trityl or tert.-butoxycarbonyl groups is anhydrous trifluoroacetic acid or aqueous formic or acetic acids. The zinc-acetic acid system is preferably used to remove the trichloroethyl group and the catalytic hydrogenation is preferably used to remove benzyl, dibenzyl or carbobenzyloxy groups.

The reaction of the products of formulae IV and V is preferably effected in water or a water-acetone mixture but equally useful are other aqueous solvents such as water-dioxane, water-tetrahydrofuran or water-ethanol.

In the case of the product of formula IV where A' is hydrogen or the product of formula V where B is hydrogen or the case where A' and B are both hydrogen, the preferred mode converts the acids in situ to the alkali metal salt of formula IV and/or V. The preferred alkali metals are sodium or potassium and they are preferably used in the form of their bicarbonates. However, other alkaline bases such as sodium hydroxide, potassium hydroxide or sodium or potassium carbonate are equally useful.

The reaction of the products of formulae IV and V is preferably effected in the presence of a buffering agent to keep the pH of the medium substantially neutral. Such a buffering agent is monosodium phosphate-sodium bicarbonate. To form the free acid of formula I, the alkali metal salts are preferably treated with acetic acid, but other mineral or organic acids such as hydrochloric acid, sulfuric acid, formic acid, oxalic acid or trifluoroacetic acid may also be used.

In the case where the compound of formula IV in which A' is an alkali metal and R is hydrogen and the compound of formula V in the alkali metal salt form are reacted in stoichiometric amounts, the acetic acid freed during the reaction can permit the products of formula Ib to crystallize in the form of an internal salt, thus rendering unnecessary the use of an acid as discussed above.

The salification of free acids of formula I may be effected by known methods such as reaction of the acids with a mineral base like sodium or potassium hydroxide or sodium bicarbonate or an organic base such as triethylamine. The salification may be effected in one or more solvents such as water, ether, ethanol or acetone.

The novel antibiotic compositions of the invention are comprised of an antibiotically effective amount of at least one compound of formula I and an inert pharmaceutical carrier. The compositions may be in the form of tablets, dragees, gelules, granules, suppositories, injectable solutions or suspensions, pomades, creams and gels prepared in the usual manner.

Examples of suitable excipients or carriers are talc, arabic gum, lactose, starch, magnesium stearate, cacao butter, aqueous and non-aqueous vehicles, fatty bodies of animal or vegetable origin, paraffinic derivatives, glycols, preservatives and diverse wetting agents, dispersants and emulsifiers.

The compositions are effective against gram positive bacteria such as staphylococcus, streptococcus and especially penicillin-resistant staphylococcus as well as against gram negative bacteria especially coliform bacteria, proteus and klebsiellae.

The compositions are therefore useful in the treatment of staphylococcia such as septicemia of staphylococcus, staphylococcia malignant on the face or skin, pyodermititis, septic or suppurantes sores, antrax, phlegmons, eresipels, acute primitive or post-grip staphylococcia, bromchopneumonia or pulmonary suppurations. They are equally useful for the treatment of collibacillosis and associated infections, infections of Proteus and Klebsiella and other affections caused by gram negative bacteria.

The novel method of combatting bacterial infections in warm-blooded animals, including humans, comprises administering to warm-blooded animals an antibacterially effective amount of at least one compound of formula I. The compounds may be administered orally, rectally, parenterally or locally by topical application to the skin or mucous. The usual effective daily dose is 5 to 80 mg/kg depending on the specific compound, the bacteria and the route of administration.

The starting materials of formula II are prepared by reacting a compound of formula V with 7-amino-cephalosporanic acid. The products of formula II wherein $R_1$ is alkyl of 1 to 4 carbon atoms and especially 7- amino-3-acetylthiomethylceph-3-eme-4-carboxylic acid are novel products.

The products of formula III are prepared by classical reactions of protection of amine functions applied to 2-amino-4-thiazolyl-acetic acid or its esters. The products of formula IV are prepared by reacting a compound of formula III with 7-amino-cephalosporanic acid followed by acid hydrolysis.

The products of formula V that are not known may be prepared by the reaction of sodium sulfhydrate with the acid chloride of the formula $R_1COCl$ according to the method described in J. Antibiotics, 27-8-577 (1974).

The products of Example 4 may exist in the form indicated or in the form of 7-[2-(2-amino-4-thiazolyl)acetamido]-3-[{(2-hydroxy-4-thiazolyl) carbonyl}-thiomethyl]ceph-3-eme-4-carboxylic acid.

In the following examples there are described several preferred embodiments to illustrate the invention. However, it is to be understood that the invention is not intended to be limited to the specific embodiments.

EXAMPLE 1

7-[2-(2-tritylamino-4-thiazolyl)-acetamido]-3-acetylthiomethyl-ceph-3-eme-4-carboxylic acid STEP A: 2-tritylamino-4-thiazolyl-acetic acid A mixture of 930 mg of ethyl 2-amino-4-thiazolyl-acetate, 25 ml of dry chloroform, 0.8 ml of triethylamine and 1.65 g of trityl chloride was stirred for 3 hours and then 3 ml of N hydrochloric acid and 5 ml of water were added thereto. The mixture was stirred and decanted and 5 ml of N hydrochloric acid and 5 ml of water were again added. The mixture was decanted and the organic phase was dried and evaporated to dryness. The residue was added to 10 ml of dioxane and 6 ml of N sodium hydroxide and the mixture was stirred at 50° C and then stood overnight at room temperature. The mixture was evaporated to dryness and the residue was diluted with water. The solution was washed with ether and was acidified with 0.5 ml of acetic acid. The mixture was allowed to crystallize and was then vacuum filtered to obtain 1.33 g of 2-tritylamino-4-thiazolylacetic acid which after empasting with ether melted at 220° C.

STEP B:
7-[2-(2-tritylamino-4-thiazolyl)-acetamido]-3-acetoxymethyl-ceph-3-eme-4-carboxylic acid A mixture of 801 mg of 2-tritylamino-4-thiazolyl-acetic acid, 10 ml of dry tetrahydrofuran and 2 ml of 1M solution of N-methyl-morpholine in tetrahydrofuran was stirred and cooled to -20° C and 2 ml of a 1M solution of isobutyl chloroformate in tetrahydrofuran were slowly added thereto. The mixture was stirred and then a solution of 544 mg of 7-amino-cephalosporanic acid in 24 ml of a 1 M solution of N-methyl-morpholine in tetrahydrofuran and 10 ml of water was added thereto. The mixture was stirred with reheating and the solvent was evaporated. The residue was diluted with water and 2 ml of 2N hydrochloric acid were added. The mixture was vacuum filtered to obtain 1.16 g of 7-[2-(2-tritylamino-4-thiazolyl)-acetamido]-3-acetoxy methyl-ceph-3-eme-4-carboxylic acid.

STEP C:
7-[2-(2-tritylamino-4-thiazolyl)-acetamido]-3-acetyl thiomethyl-ceph-3-eme-4-carboxylic acid A mixture of 1.63 of the product of Step B, 0.21 g of sodium bicarbonate, 0.66 g of potassium thioacetate, 10 ml of water and 5 ml of acetone was heated at 90° C for 2½ hours and was then acidified with 1 ml of acetic acid. The mixture was vacuum filtered and the solid product was washed and chromatographed over silica gel. Elution with a 1-1 methylene chloride-ether mixture and then with a 5-1-4 acetone-water-ether mixture yielded 830 mg of 7-[2-(2-tritylamino-4-thiazolyl)-acetamido]-3-acetylthiomethyl-ceph-3-eme-4-carboxylic acid.

EXAMPLE 2

7-[2-(2-amino-4-thiazolyl)-acetamido]-3-acetylthiomethyl-ceph-3-eme-4-carboxylic acid The product of Example 1 in 50% aqueous formic acid was heated at 60° C for 15 minutes and the formic acid was evaporated. The residue was taken up in acetone and the mixture was vacuum filtered to obtain 325 mg of product. The latter was dissolved in 2.6 ml of acetone containing 20% of water and 0.3 ml of 2N hydrochloric acid and the mixture was vacuum filtered. 3 drops of pyridine and 1 ml of acetone were added to the filtrate to obtain 0.228 mg of purified 7-[2-(2-amino-4-thiazolyl)-acetamido]-3-acetylthiomethyl-ceph-3-eme-4-carboxylic acid.

Analysis: $C_{15}H_{16}O_5N_4S_3$: Calculated: %C, 42.04; %H, 3.76; %N, 13.07; %S, 22.44. Found: %C, 41.7; %H, 3.9; %N, 12.8; %S, 20.9.

EXAMPLE 3

7-[2-(2-tritylamino-4-thiazolyl)-acetamido]-3-acetylthiomethyl-ceph-3-eme-4-carboxylic acid STEP A:
7amino-3-acetylthiomethyl-ceph-3-eme-4-carboxylic acid A mixture of 5.44 g of 7-amino-cephalosporanic acid and 50 ml of water with 1% hydroquinone was stirred under an inert atmosphere and 1.7 g of sodium bicarbonate were added thereto. After dissolution occurred, 3 g of potassium thioacetate were added thereto and the mixture was heated for 3 hours at 60° C and then was cooled. The mixture was acidified with acetic acid and stirred at room temperature and then vacuum filtered. The recovered product was washed and dried to obtain 4.9 g of 7-amino-3-acetylthiomethyl-ceph-3-eme-4-carboxylic acid.

STEP B:
7-[2-(2-tritylamino-4-thiazolyl)-acetamido]-3-acetylthiomethyl-ceph-3-eme-4-carboxylic acid A mixture of 9.9 g of 2-tritylamino-4-thiazolylacetic acid, 100 ml of tetrahydrofuran and 2.7 ml of N-methyl-morpholine was stirred under an inert gas for 15 minutes at room temperature and was then cooled to -15° C after which 3.15 ml of isobutyl chloroformate were added. The mixture was stirred for 5 minutes at -10° to -15° C and then 6.5 g of the product of Step A, 65 ml of water and 3.15 ml of triethylamine were added over 2 minutes. The mixture was stirred for 1½ hours at room temperature and the tetrahydrofuran was removed. The mixture was acidified and was extracted with methylene chloride. The mixture was vacuum filtered and the organic phase was washed and evaporated to dryness. The powdery residue was triturated with ether and dried to obtain 15.2 g of raw product. 6.7 g of of the said product were dissolved in methylene chloride and ethyl acetate was added thereto. The insoluble phase was removed and the solution was treated with carbon black and was vacuum filtered. The recovered product was rinsed and dried to obtain 5.1 g of 7-[2-(2-tritylamino-4-thiazolyl)-acetamido]-3-acetylthiomethyl-ceph-3-eme-4-carboxylic acid.

EXAMPLE 4

7-[2-(2-amino-4-thiazolyl)-acetamido]-3-[{(2-oxo-(3H)-thiazolin-4-yl)-carbonyl}-thiomethyl]-ceph-3-eme-4-carboxylic acid

STEP A:
7-[2-(2-amino-4-thiazolyl)-acetamido]-3-acetoxymethyl-ceph-3-eme-4-carboxylic acid A mixture of 351 mg of 7-[2-(2-tritylamino-4-thiazolyl)-acetamido]-3-acetoxymethyl-ceph-3-eme-4-carboxylic acid 0.44 ml of acetic acid and 0.22 ml of water was heated to 60° C and was stirred for 40 minutes and then cooled. The mixture was diluted with acetone and then with ether and was vacuum filtered. The precipitate was dried to obtain 171 mg of raw product.

470 mg of the said product were dissolved in 5 ml of a refluxing 1-1 mixture of ethanol and water and the mixture was vacuum filtered. The filtrate was cooled and vacuum filtered again to obtain a first yield of 170 mg. The filtrate of the first crop was combined with the first insolubles to obtain a second yield of 107 mg for a total yield of 277 mg of 7-[2-(2-amino-4-thiazolyl)-acetamido]-3-acetoxymethyl-ceph-3-eme-4-carboxylic acid.

STEP B: (2-oxo-(3H)-thiazolin-4-yl)-thiocarboxylic acid 1.635 g of (2-oxo-(3H)-thiazolin-4-yl)-carboxylic acid chloride were added to a mixture of 1.6 g of 70% sodium sulfhydrate, 16 ml of ethanol and 2.5 ml of water at 10° C and the mixture was stirred for an hour. The ethanol was evaporated and water was added to the reaction mixture. 0.8ml of concentrated hydrochloric acid were added with stirring and the mixture was vacuum filtered. The recovered product was rinsed and dried to obtain 1.46 g of (2-oxo-(3H)-thiazolin-4-yl)-thiocarboxylic acid.

STEP C:
7-[2-(2-amino-4-thiazolyl)-acetamido]-3-[{(2-oxo-(3H)-thiazolin-4yl)-carbonyl}thiomethyl]-ceph-3-eme-4-carboxylic acid A mixture of 0.825 g of the product of Step A, 4 ml of distilled water, 0.4 g of the product of Step B, 0.39 g of monosodium phosphate and 0.21 g of sodium bicarbonate was stirred for 5 hours at 50° C and was then cooled. Acetic acid was added thereto to adjust the pH to 4 to 5 and the mixture was vacuum filtered to obtain after drying 0.56 g of raw product. The latter was dissolved in 5 ml of water containing an equivalent of sodium bicarbonate and the solution was passed through an ion exchange resin column. The column was eluted with water and the product was recovered with water containing 10% isopropanol. The fractions were combined and acidified with acetic acid to obtain 0.12 g of 7-[2-(2-amino-4-thiazolyl)-acetamido]-3-[{(2-oxo-(3H)-thiazolin-4-yl)-carbonyl}thiomethyl]-ceph-3-eme-4-carboxylic acid.

UV spectrum (ethanol containing 10% HCl): Max. at 258 nm, $\epsilon$ = 16,350; Max. at 307 nm, $\epsilon$ = 10,350;

Infrared spectrum (Nujol): 1722 cm$^{-1}$ ($\beta$-lactam); 1682–1638 cm$^{-1}$ (secondary amide

EXAMPLE 5

7-[2-(2-amino-4-thiazolyl)-acetamido]-3-[{(2-furyl)-carbonyl}thiomethyl]-ceph-3-eme-4-carboxylic acid

STEP A: sodium 7-[2-(2-amino-4-thiazolyl)-acetamido]-3-acetoxymethyl-ceph-3-eme-4-carboxylate A mixture of 2.26 g of 7-[2-(2-amino-4-thiazolyl)-acetamido]-3-acetoxymethyl-ceph-3-eme-4-carboxylic acid, 420 mg of sodium bicarbonate, 10 ml of water and 0.5 g of activated carbon was stirred for 3 minutes at 50° C and was then vacuum filtered. The filtrate was washed with acetone and concentrated to 5 ml and 50 ml of acetone were added. The mixture was heated to 60° C to cause crystallization and was vacuum filtered to obtain 1.745 g of sodium 7-[2-(2-amino-4-thiazolyl)-acetamido]-3-acetoxymethyl-ceph-3-eme-4-carboxylate with a specific rotation of $[\alpha]_D = +120°$ (C = 1% in water).

STEP B:
7-[2-(2-amino-4-thiazolyl)-acetamido]-3-[{(2-furyl)carbonyl}thiomethyl]-ceph-3-eme-4-carboxylic acid A mixture of 0.25 g of 2-furyl-thioacetic acid, 4 ml of distilled water, 0.17 mg of sodium bicarbonate and 0.435 mg of the salt of Step A was held at 50° C for 5 hours and was then cooled to room temperature. The mixture was adjusted to a pH of 3-4 with acetic acid and was vacuum filtered. The recovered product was rinsed and dried to obtain 420 mg of raw product. The latter was dissolved in water containing sodium hydroxide and the solution was passed through an ion exchange resin column. Elution was with water and then with water containing 10% of isopropanol and the fractions with the product were combined and the solvents were evaporated under reduced pressure. The aqueous residue was acidified with acetic acid to obtain 115 mg of 7-[-(2-amino-4-thiazolyl)-acetamido]-3-[{(2-furyl)-carbonyl}•thiomethyl]-ceph-3-eme-4-carboxylic acid.

Analysis: $C_{18}H_{16}O_6N_4S_3$: Calculated: %C, 45.0; %H, 3.4; %N, 11.7; %S, 20.0. Found: %C, 44.5; %H, 3.5; %N, 12.2; %S, 20.0.

EXAMPLE 6

7-[2-(2-amino-4-thiazolyl)-acetamido]-3-propionylthiomethyl-ceph-3-eme-4-carboxylic acid 128 ml of ethanol were added to a mixture of 4.6 ml of propionyl chloride in a solution of 8 g of sodium sulfhydrate in 20 ml of water and the mixture was stirred for 30 minutes and was vacuum filtered. The filtrate was evaporated to dryness and the residue was taken up in ethanol. The solution was evaporated again and the residue was again taken up in ethanol. The mixture was vacuum filtered and the filtrate was evaporated to dryness. The residue was added to ether and vacuum filtered to obtain 4.5 g of sodium thiopropionate.

A mixture of 1.23 g of 7-[-2-(2-amino-4-thiazolyl)acetamido]-3-acetoxymethyl-ceph-3-eme-4-carboxylic acid, 12ml of water, 252 mg of sodium bicarbonate and 516 mg of sodium thiopropionate was heated at 60° C for 4 hours and was then cooled. 0.2 g of carbon black were added to the mixture which was then vacuum filtered. The product was acidified, washed and dried to obtain 0.88 g of raw product. 0.44 g of the raw product in 8.6 ml of methylene chloride and 0.2 ml of triethylamine was stirred and then was vacuum filtered. The insolubles were re-extracted and vacuum filtered again. The combined filtrates were evaporated to dryness and the residue was dissolved in water. 0.2 ml of acetic acid were added to the solution and the mixture was vacuum filtered. The recovered product was washed and dried to obtain 0.232 g of purified 7-[2-(2-amino-4-thiazolyl)-acetamido]-3-propionylthiomethyl-cep-3-eme-4-carboxylic acid.

Analysis: $C_{16}H_{18}O_5N_4S_3$: Calculated: %C, 43.42; %H, 4.1; %N, 12.66; %S, 21.73. Found: %C, 43.3; %H, 4.3; %N, 12.2; %S, 20.8.

EXAMPLE 7

An injectable solution was prepared from 500 mg of 7-[2-(2-amino-4-thiazolyl)-acetamido]-3-acetylthiomethyl-ceph-3-eme-4-carboxylic acid and sufficient sterile aqueous excipient for a total volume of 5 ml. Gelules were prepared with 250 mg of the same product and sufficient excipient for a gelule with a final weight of 400 mg.

PHARMACOLOGICAL DATA

A. In Vitro Activity — Dilution Method in Liquid Media

A series of tubes were prepared with the same quantity of sterile nutrive media and increasing quantities of the test product was distributed to each tube. Then, each tube was seeded with a bacterial strain and after incubation at 37° C for 24 or 48 hours, the inhibition of the growth was determined by transillumination which permitted determination of the minimum inhibitory concentrations (M.I.C.) in μg/ml. The results are reported in Tables I to IV.

TABLE I

| PRODUCT - EXAMPLE 2 | | |
| --- | --- | --- |
| | MIC in μg/ml | |
| Bacterial Strain | 24 H | 48 H |
| Staphylococcus Oxford UC 1061 Penicillin sensible | 0.5 | 0.5 |
| Staphylococcus aureus UC 1128 Penicillin resistant | 1 | 1 |
| Streptococcus hemolyticus (in bacto Todd Hewitt Broth pH = 7.8) | 0.05 | 0.1 |
| Streptococcus faecalis n° 5 432 | 5 | >40 |
| Bacillus subtilis | 0.1 | 0.5 |
| Escherichia Coli UC 1 020 | 2 | 5 |
| Escherichia Coli UC 1 261 | 1 | 1 |
| Klebsiella pneumoniae 52 145 | 0.5 | 0.5 |
| Proteus mirabilis (indol) | 1 | 1 |
| Staphylococcus aureus 54 146 | 0.6 | 0.6 |
| Escherichia Coli (T) 0 26 B 6 | 3 | 3 |

TABLE II

| PRODUCT - EXAMPLE 4 | | |
| --- | --- | --- |
| | MIC in μg/cm³ | |
| Bacterial Strain | 24 H | 48 H |
| Staphylococcus aureus UC 1 061 Penicillin sensible | 0.2 | 0.5 |
| Staphylococcus aureus UC 1 128 Penicillin resistant | 1 | 1 |
| Staphylococcus aureus n° 54 146 | 0.5 | 1 |
| Streptococcus pyogenes A 561 | 0.1 | 0.2 |
| Streptococcus faecalis 5 432 | 10 | >40 |
| Bacillus subtilis | 0.1 | 0.1 |
| Escherichia Coli UC 1 020 | 2 | 2 |
| Escherichia Coli UC 1 261 | 1 | 1 |
| Escherichia Coli T 026 B 6 | 2 | 3 |
| Escherichia Coli R 55 123 D | 5 | 10 |
| Klebsiella Pneumoniae 52 145 | 0.1 | 0.2 |

TABLE II-continued

| PRODUCT - EXAMPLE 4 | | |
| --- | --- | --- |
| | MIC in μg/cm³ | |
| Bacterial Strain | 24 H | 48 H |
| Proteus mirabilis (indol) A 235 | 0.6 | 0.6 |
| Salmonella Typhimurium 420 | 3 | 3 |

TABLE III

| PRODUCT - EXAMPLE 5 | | |
| --- | --- | --- |
| | MIC in μg/cm³ | |
| Bacterial Strain | 24 H | 48 H |
| Staphylococcus aureus UC 1 061 Penicillin sensible | 0.5 | 1 |
| Staphylococcus aureus UC 1 128 Penicillin resistant | 1 | 2 |
| Staphylococcus aureus n° 54 146 | 1 | 1 |
| Streptococcus pyogenes A 561 | 0.1 | 0.1 |
| Streptococcus faecalis 5 432 | 5 | 40 |
| Bacillus subtilis ATCC 6 633 | 0.2 | 0.2 |
| Staphylococcus aureus ATCC 6 538 | 0.5 | 1 |
| Escherichia Coli ST UC 1 020 | 10 | 10 |
| Escherichia Coli RT UC 1 261 | 2 | 2 |
| Escherichia Coli T 026B6 | 10 | 10 |
| Escherichia Coli RG R 55 123 D | 10 | 10 |
| Klebsiella pneumoniae Exp. 52 145 | 0.4 | 1 |
| Proteus mirabilis (Indol) A 235 | 2 | 2 |
| Salmenella Typhimurium 10 | 10 | |

TABLE IV

| PRODUCT - EXAMPLE 6 | | |
| --- | --- | --- |
| | MIC in μg/cm³ | |
| Bacterial Strain | 24 H | 48 H |
| Staphylococcus aureus UC 1 061 Penicillin sensible | 0.6 | 0.6 |
| Staphylococcus aureus UC 1 128 Penicillin resistant | 1 | 1 |
| Staphylococcus aureus 54 146 | 1 | 2 |
| Streptococcus pyogenes A 561 | 0.2 | 0.2 |
| Streptococcus faecalis 99 F 74 | 20 | 40 |
| Bacillus subtilis ATCC 6 633 | 0.1 | 0.1 |
| Staphylococcus aureus ATCC 6 538 | 0.2 | 0.4 |
| Escherichia Coli ST UC 1 020 | 10 | 10 |
| Escherichia Coli RT UC 1 261 | 10 | 10 |
| Escherichia Coli T 026B6 | 40 | 40 |
| Klebsiella pneumoniae 52 145 | 3 | 5 |
| Proteus mirabilis (Indol ) A 235 | 10 | 20 |
| Salmonella Typhimurium 420 | 5 | 5 |
| Serratia RG 2 532 | 10 | 10 |

B. In Vivo Activity — Experimental Staphylococcia

The antibacterial activity of the compound of Example 2 was determined against experimental staphylococcia in mice. Lots of 10 male mice weighing about 21.5 g were infected by intraperitoneal injection of 0.5 ml of a 24 hour culture of staphylococcus aureus 54,146 in Pasteur nutritive broth diluted by 1/5 with distilled water. The test product was administered subcutaneously 1 hour, 5 hours and 24 hours after the infection in different doses. The number of dead mice was determined during 8 days and the results are reported in Table V.

TABLE V

| Dose administered in each injection | Mortality after | | | | | | Mice living after 8th day |
| --- | --- | --- | --- | --- | --- | --- | --- |
| | 9 h 45 | 22 h 30 | 25 h 30 | 29 h | 4 d | 5 d | |
| 0.1 mg | 1 | 8 | | 1 | | | 0/10 |
| 0.25 mg | | 1 | 1 | | 1 | 1 | 6/10 |
| 0.5 mg | | | | | 1 | | 9/10 |
| 0.75 mg | | | | | | | 10/10 |
| 1 mg | | | | | | | 10/10 |

C. In Vivo Activity — Experimental Infection of Proteus Mirabilis

The product of Example 2 was studied for its effect on an experimental infection of Proteus mirabilis in mice. Groups of 10 male mice weighing about 22.5 g were infected by an intraperitoneal injection of 0.5 ml of a 24 hour culture in Pasteur nutritive media of Proteus mirabilis No. A 235 diluted by ¼ with distilled water.

The mice received a subcutaneous injection 1 hour, 5 hours and 24 hours after the infection of a quantity of the product of Example 2 and the mortality was noted during 8 days. The results are in Table VI.

TABLE VI

| Dose administered in each injecton | Mortality after 21 h 15 | Mice living on 8th day |
|---|---|---|
| Controls | 10 | 0/10 |
| 0.1 mg | 2 | 8/10 |
| 0.25 mg | 0 | 10/10 |
| 0.5 mg | 0 | 10/10 |
| 0.75 mg | 0 | 10/10 |

D. Experimental Infection with Escherichia Coli (T) 026B6

Again, the activity of the product of Example 2 was tested against experimental infection of Escherichia Coli in mice. Groups of 10 male mice weighing about 23 g were infected with an intraperitoneal injection of 0.5 ml of a 24 hour culture in Pasteur nutritive media of Escherichia Coli (T) 026B6 diluted by 1/6 with distilled water. The test product was administered subcutaneously one hour, five hours and 24 hours after the infection and the mortality was determined during 8 days. The results are reported in Table VII.

TABLE VII

| Dose Admininstered in each injection | 21 h 15 | 24 h 15 | 27 h 45 | 30 h 45 | 45 h 30 | 70 h | Mice Living on 8th day |
|---|---|---|---|---|---|---|---|
| Control | 10 | | | | | | 0/10 |
| 0.5 mg | 6 | 1 | 1 | | 1 | 1 | 0/10 |
| 1 mg | | | | 1 | | | 9/10 |
| 2 mg | | | | | | | 10/10 |
| 3 mg | | | | | | | 10/10 |

The results of Tables I to VII clearly show the antibacterial activity of the tested compounds.

Various modifications of the products and methods of the invention may be made without departing from the spirit or scope thereof and it should be understood that the invention is to be limited only as defined in the appended claims

I claim:

1. 7-amino-thiazolyl-acetamido-cephalosporanic acid compounds of the formula

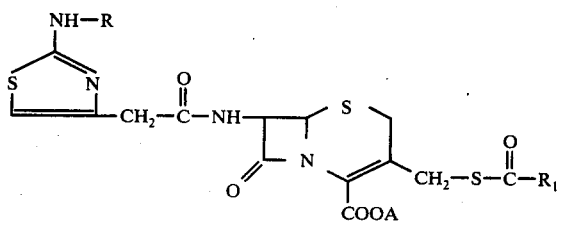

wherein R is selected from the group consisting of hydrogen, tert.-butoxy carbonyl, trityl, benzyl, dibenzyl, trichloroethyl, carbobenzyloxy, formyl and phthaloxy, $R_1$ is selected from the group consisting of alkyl of 1 to 4 carbon atoms, furyl, thiazolyl, oxothiazolinyl, isothiazolyl, oxazolyl, imidazolyl, diazolyl, thiadiazolyl and tetrazolyl, and A is selected from the group consisting of hydrogen, alkali metal and equivalents of alkaline earth metals, magnesium and a non-toxic, pharmaceutically acceptable organic amine.

2. A compound of claim 1 wherein R is selected from the group consisting of tert.-butoxycarbonyl, trityl, dibenzyl, trichloroethyl and carbobenzyloxy.

3. A compound of claim 1 wherein R is selected from the group consisting of hydrogen and trityl, A is hydrogen and $R_1$ is selected from the group consisting of methyl, ethyl, furyl and 2-oxo (3H) thiazolin-4-yl.

4. A compound of claim 1 which is 7-[2-(2-amino-4-thiazolyl)-acetamido]-3-acetylthiomethyl-ceph-3-eme-4-carboxylic acid.

5. A compound of claim 1 which is 7-[2-(2-amino-4-thiazolyl)-acetamido]-3-[{(2-oxo (3H) thiazolin-4-yl) carbonyl}thiomethyl]-ceph-3-eme-4-carboxylic acid.

6. A compound of claim 1 which is 7-[2-(2-amino-4-thiazolyl)-acetamido]-3-[{(2-furyl)-carbonyl}thiomethyl]-ceph-3-eme-4-carboxylic acid.

7. A compound of claim 1 which is 7-[2-(2-amino-4-thiazolyl)-acetamido]-3-[propionylthiomethyl]-ceph-3-eme-4-carboxylic acid.

8. An antibiotic composition comprising an antibiotically effective amount of at least one compound of claim 1 and an inert pharmaceutical carrier.

9. A composition of claim 8 wherein R is selected from the group consisting of tert.-butoxycarbonyl, trityl, dibenzyl, trichloroethyl and carbobenzyloxy.

10. A composition of claim 8 wherein R is selected from the group consisting of hydrogen and trityl, A is hydrogen and $R_1$ is selected from the group consisting of methyl, ethyl, furyl and 2-oxo (3H) thiazolin-4-yl.

11. A composition of claim 8 wherein the compound is 7-/2-(2-amino-4-thiazolyl)-acetamido/-3-acetylthiomethyl-ceph-3-eme-4-carboxylic acid.

12. A method of combatting bacterial infections in warm-blooded animals comprising administering to warm-blooded animals an antibacterially effective amount of at least one compound of claim 1.

13. The method of claim 12 wherein R is selected from the group consisting of tert.-butoxycarbonyl, trityl, dibenzyl, trichloroethyl and carbobenzyloxy.

14. The method of claim 12 wherein R is selected from the group consisting of hydrogen and trityl, A is hydrogen and $R_1$ is selected from the group consisting of methyl, ethyl, furyl and 2-oxo (3H) thiazolin-4-yl.

15. The method of claim 12 wherein the compound is 7-[2-(2-amino-4-thiazolyl)-acetamido]-3-acetylthiomethyl-ceph-3-eme-4-carboxylic acid.

* * * * *